United States Patent [19]

Walker et al.

[11] Patent Number: 5,115,686
[45] Date of Patent: May 26, 1992

[54] VAPOR FREE MULTI-LIQUID SAMPLER

[75] Inventors: R. David Walker, Okmulgee; David A. Scheidt, Sapulpa, both of Okla.

[73] Assignee: Conoco Inc., Ponca City, Okla.

[21] Appl. No.: 487,558

[22] Filed: Mar. 2, 1990

[51] Int. Cl.⁵ .............................................. G01N 1/16
[52] U.S. Cl. ................................................ 73/863.31
[58] Field of Search ............ 73/863.31, 865.8, 863.71, 73/863.81, 863.83, 863.86, 864.81, 440, 444–454

[56] References Cited

U.S. PATENT DOCUMENTS

| | | | |
|---|---|---|---|
| 65,078 | 5/1867 | Hart | 73/445 |
| 2,023,196 | 12/1935 | Fairchild | 73/445 |
| 2,595,311 | 5/1952 | Strange et al. | |
| 3,362,222 | 1/1968 | Johnson et al. | |
| 4,077,265 | 3/1978 | Strain | 73/445 |
| 4,454,772 | 6/1984 | Brunner et al. | |
| 4,454,773 | 6/1984 | Brunner et al. | |
| 4,702,109 | 10/1987 | Viola | 73/440 |

OTHER PUBLICATIONS

Densitrol Brochere, Princo, Southhampton, PA. Aug. 1965, Bulletin W-11.

*Primary Examiner*—Robert Raevis

[57] ABSTRACT

A vapor tight sampler which is used to visually examine flowing liquid or liquids to determine color, gravity and solids content thereof. The sampler comprises a metal block on which are disposed a plurality of clear cylinders which are covered and gasketed at the top and gasketed to the metal block at the bottom. A pressure release plug is provided in each cover. A header is provided in the block for supplying liquid feed. A separate feed line runs from the header to the bottom of each cylinder. Disposed within each cylinder is an aspirating overflow tube to remove liquid and vapors and prevent overfilling of the cylinders. A vent line is provided in the top of each cylinder. The vent lines and overflow tubes are connected to a drain tank through the metal block. The drain tank provides egress to a separator or drain system and a vent line to the atmosphere. Openings are provided in the block below each cylinder for draining purposes. Three way valves are provided in each feed line and also connect with each drain from the cylinders so that it is possible to fill each cylinder, drain each cylinder or both drain and fill each cylinder at the same time with a single valve. During operation of the sampler, a hydrometer is placed in each cylinder with each hydrometer being designed to reflect the gravity of only one of the liquids which are being sampled.

17 Claims, 5 Drawing Sheets

VAPOR FREE MULTI-LIQUID SAMPLER

BACKGROUND OF THE INVENTION

Petroleum fluids are often transported from one location to another through pipelines. Usually more than one fluid is moved through a single pipeline, for example, gasolines of various grades, kerosene, jet fuel, and diesel fuel, may all be moved through a single pipeline in any order or sequence. The gasolines transported through pipelines may be either regular gasoline, unleaded, or super unleaded. When two fluids are transferred through a pipeline in sequence, there is usually mixing at the interface of the two fluids so that each fluid contaminates the other. When pipelining of the fluids is completed, this contaminated material must be separated to keep the individual products in specification.

The operator of the pipeline must know at all times what product is flowing through the pipeline at any given location so that he can carry out appropriate switching to be sure that products are placed in correct storage or directed to the correct terminals.

Identification of liquids flowing through a pipeline is made by pulling samples periodically. Since only a few products are handled in the pipeline, usually from two to five products, it is easy to identify each particular product by a gravity measurement. Gravity is customarily determined by a hydrometer. The mixed material at the interface between two liquids may also be identified by gravity and color. The operator is also concerned with cleanliness of the flowing liquids and whether or not the liquids contain any solids. All of the above information may readily be obtained by visual examination of the liquid samples.

Environmental concerns dictate that personnel drawing samples from a pipeline not be exposed to dangerous chemicals. Among such chemicals is benzene which is often present in small amounts in gasolines, which are a primary pipeline petroleum product.

It is of great importance to provide a sampling system which is vapor tight and which provides the necessary means for visual evaluation of pipeline petroleum liquids.

PRIOR ART

U.S. Pat. No. 3,362,222 to Johnson et al. relates to a fluid sampling apparatus and flowmeter. The apparatus consists of a plurality of fluid tight bottles substantially evacuated prior to use, each of which is in communication with an elongated tube adapted to communicate with a fluid stream from which samples are to be taken.

U.S. Pat. Nos. 4,454,772 and 4,454,773 both to Brunner et al. relate to an automatic multi-phase well fluid sampler and a method for sampling fluid, such as a produced oil-water fluid from one of a plurality of wells. The sampler contains inlet solenoid valve means for each of a plurality of a sample containers wherein each solenoid is responsive to a timing device and stopping switch means for precisely filling each sample container periodically in consecutive order.

U.S. Pat. No. 2,595,311 to Strange et al. described an automatic multiple sampling valve comprising a plurality of individual three way valve units that are actuated to control the flow of one or another of several streams of gas to equipment for testing it. The valve is contained in a metal block. CL THE INVENTION The invention comprises a vapor tight liquid sampler in which a liquid is introduced to at least one vertically disposed, clear cylinder which is enclosed at the top and is mounted on a housing. Each cylinder of the sampler contains an overflow line through which excess fluid is removed from the sampler. A vent line to the atmosphere is also attached to each cylinder. Each cylinder also contains a drain line which along with the overflow line is connected to a drain to a separator or other suitable location. Liquid sample is flowed to the cylinders at a controlled rate such that there is continuous flow of liquid into the overflow line and from the system. This continuous flow through the overflow lines causes a partial vacuum in the cylinders whereby vapors in the cylinder and outside air through the vent line are aspirated in the flowing liquid. The aspirated vapors and air are carried with the liquid into the separator system which is provided with a check valve to prevent back-up of vapors and liquids. The various cylinders contain hydrometers each of which is designed to reflect the gravity of only one of the liquids being sampled. The operator thus is able to determine which liquid has been sampled by its gravity. The operator can also visually examine the liquid sample or samples to determine color and if solids are present in the sample liquids.

The sampler is preferable comprised of a metal block and an enclosed drain tank attached to the metal block. All the connections to the vertical cylinders are made either within or from the metal block thus substantially reducing the chance for leakage into or out of the system. Connections to the drain tank are also made through the metal block which again reduced the chance of leakage. Use of the metal block and attached drain tank provides a sampler which is small in size and is readily moved from on location to another.

DETAILED DESCRIPTION OF THE INVENTION

Figure 1:
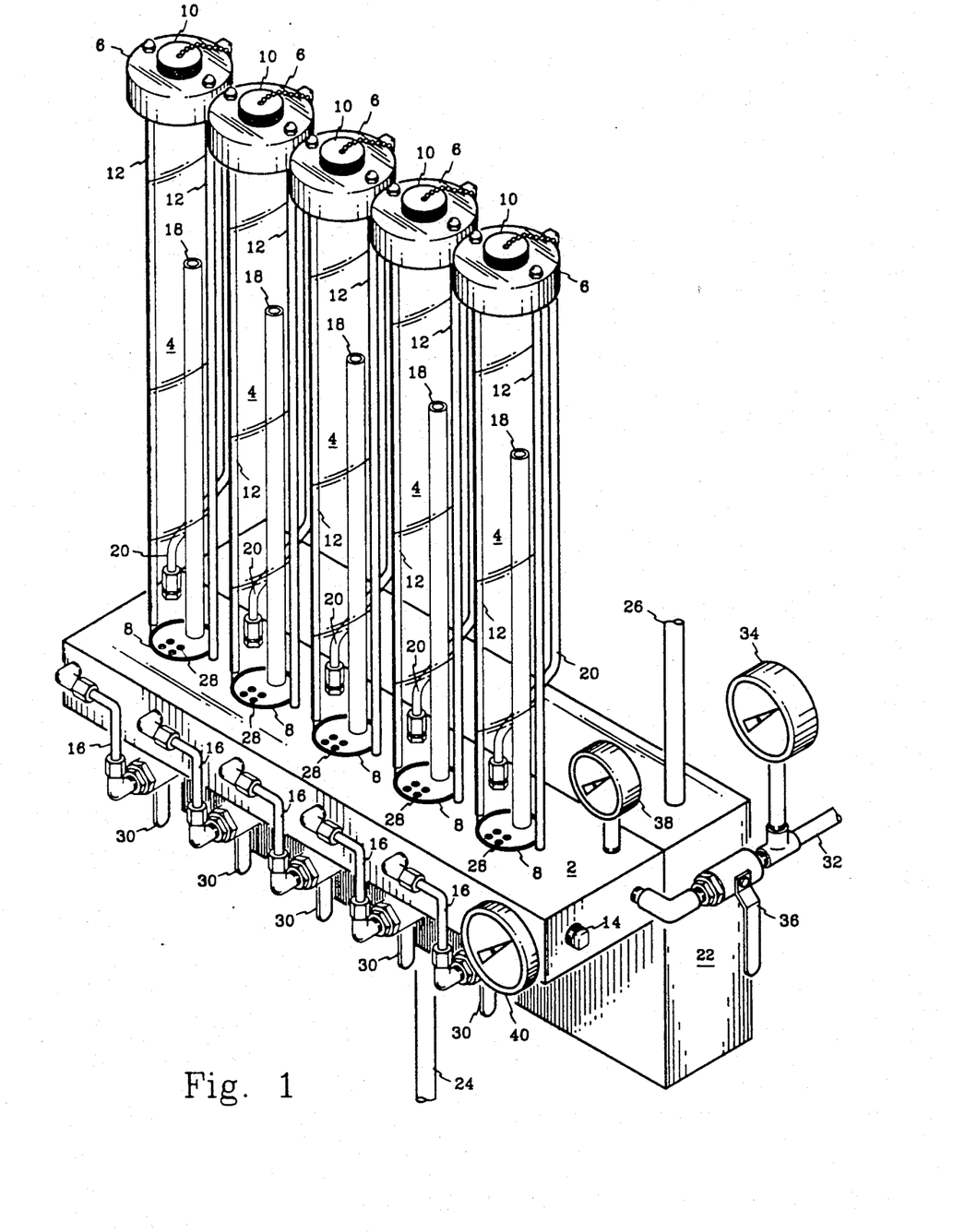
FIG. 1 is a schematic diagram illustrating a perspective view of one embodiment of the vapor-tight liquid sampler.

Referring to the drawings, FIG. 1 includes a metal block 2 upon which are disposed five clear, vertical cylinders 4. The top of each cylinder is covered with a metal closure 6 which contains a gasket, not shown, and is held in engagement with metal block 2 by two rods 12 which are screwed into the metal block. Each cylinder is fitted into a recess in the metal block which contains a gasket 8. Each top enclosure 6 contains a pressure relief plug 10 which is shown in more detail in FIGS. 5 and 6. Each cylinder 4 contains an overflow tube 18 to prevent overfilling. The overflow tubes terminate at the top in the upper portion of cylinders 4. A vent line 20 is provided in the top 6 of each cylinder. The vent lines and overflow tubes are connected to a drain tank 22 which is attached to metal block 2. The drain tank provides egress to a separator or drain system through line 24 and a vent line 26 from the atmosphere. Openings 28 are provided in block 2 below each cylinder for draining purposes. These openings which are usually several small holes, are sized to provide an emptying rate from the cylinder which is reasonably fast, but not sufficiently rapid to harm the hydrometer which is contained in each cylinder during operation of the sampler. A header 14 passes entirely through block 2. It is plugged at one end and open to receive the liquid sample at the other end. This enables installation of the sampler so that the sample feed can be introduced to either end of block 2. Feed lines 16 connect header 14 with each cylinder 4. Three-way valves of which only the handle 30 is shown, are provided in each feed line 16 and also connect with each drain 28 from the cylinders so that it is possible to fill each cylinder, drain each cylinder, or both drain and fill each cylinder at the same time with a single valve. As previously stated, during the operation of the sampler, a hydrometer is placed in each cylinder. Each hydrometer is designed to reflect the gravity of only one of the liquids which are being periodically sampled. For example, if gasoline, jet fuel, and diesel fuel are to be sampled, three cylinders 4 would be utilized in the sampling procedure. Each cylinder would contain a hydrometer and the three hydrometers would reflect the gravity of gasoline, jet fuel, and diesel fuel, respectively.

Feed to the sampler is introduced through line 32 on which is mounted pressure gauge 34 which monitors the line pressure. A valve 36 is provided in line 32 to control the flow rate to the sampler and the pressure of the liquid entering the sampler which is reflected by pressure gauge 38. Within block 2, line 32 connects with header 14 thereby providing flow of sample to one or more of cylinders 4. The temperature of the sample in the block is measured by thermometer 40 which is placed in a thermowell in contact with the fluid being sampled.

The point of introduction of sample feed through line 32 as shown is for convenience in locating pressure gauge 38. The feed could be introduced directly to header 14 and pressure gauge 38 located either in line 32 following valve 36 or in block 2, either upstream or downstream of thermometer 40.

Figure 2:
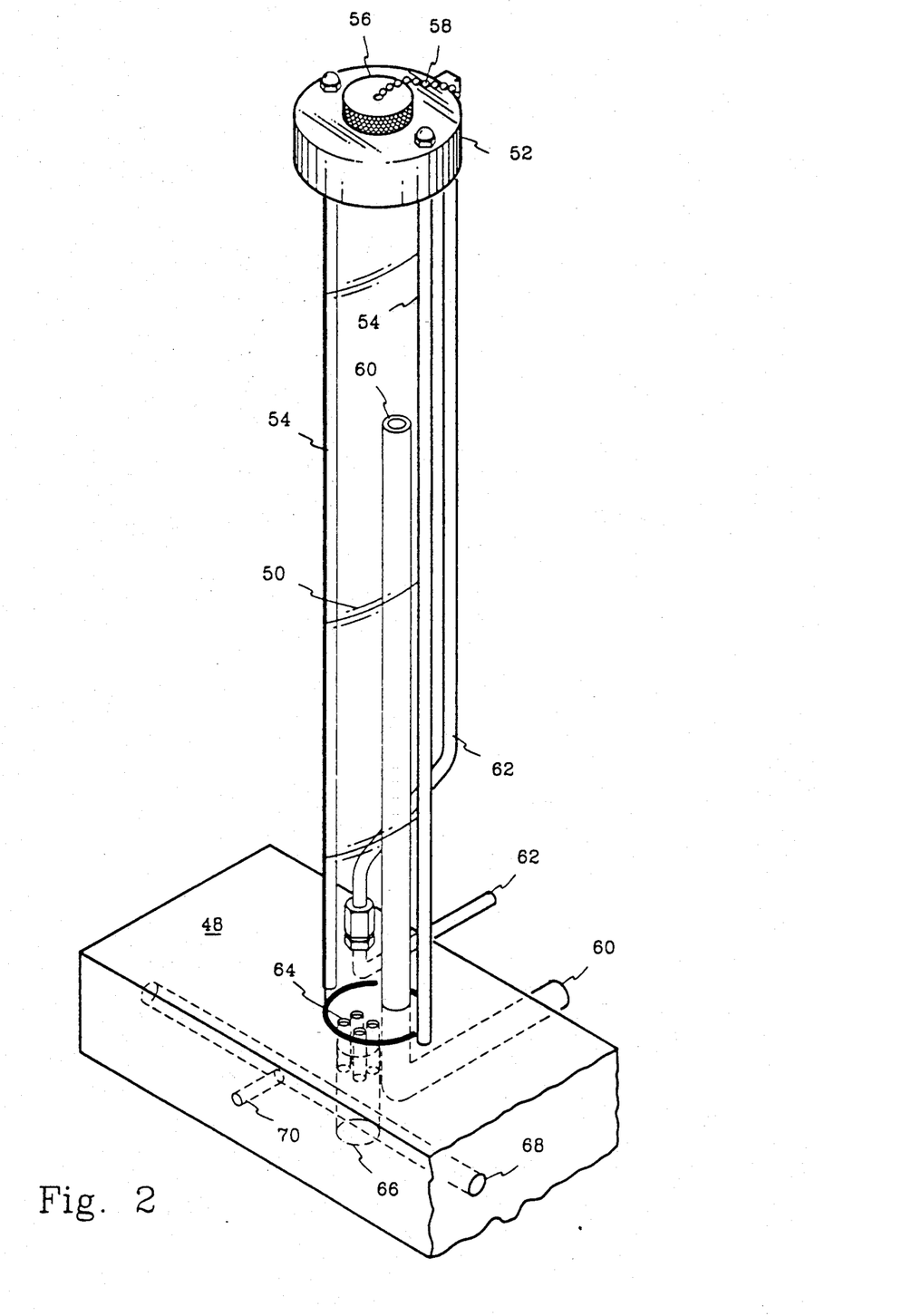
FIG. 2 is an enlarged perspective of a single vertical cylinder with associated piping and attachments, as illustrated in the sampler of FIG. 1.

FIG. 2 shows an enlarged view of a portion of the sampler in which 48 is the end portion of the metal block and 50 is a vertically disposed clear cylinder. The top of cylinder 50 is sealed with a cover 52 which holds cylinder 50 securely to block 48 with rods 54. Disposed within the top of cover 52 is a pressure relief plug 56 which is attached to 52 with chain 58 or other suitable means. Pressure relief plug 56 fits snugly into an opening in cover 52 which opening is of sufficient size to allow introduction and removal of a hydrometer. A vent line 62 is provided from the top of cover 52 and passes through the top of block 48 and into an adjacent drain tank (not shown). Overflow tube 60 also passes through the top of block 48 and terminates in the same drain tank. Draining of cylinder 50 is effected through holes 64 which terminate in a larger drain line 66 passing through and exiting from the bottom of block 48. Feed to the sampler is introduced through header 68, line 70 and a three-way valve, as previously described (not shown).

Figure 3:
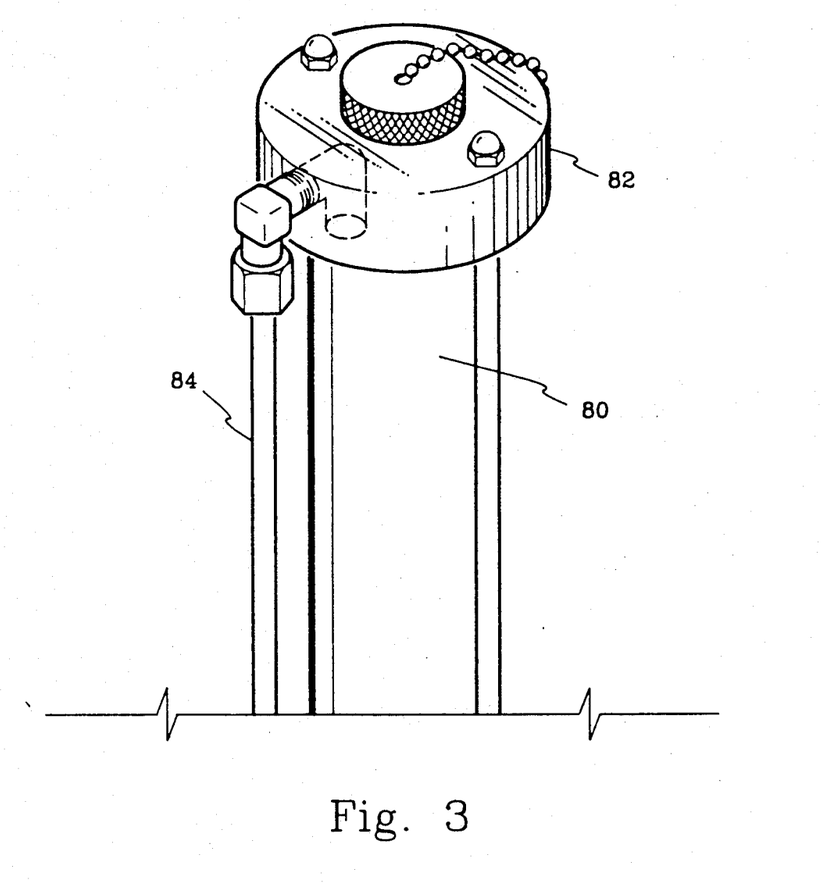
FIG. 3 further illustrates the location of the vent line shown in FIG. 2.

FIG. 3 illustrates in more detail, the location of the vent line in the cylinder cover. In this figure, the cylinder is designated by 80, the cylinder cover by 82 and the vent line by 84.

Figure 4:
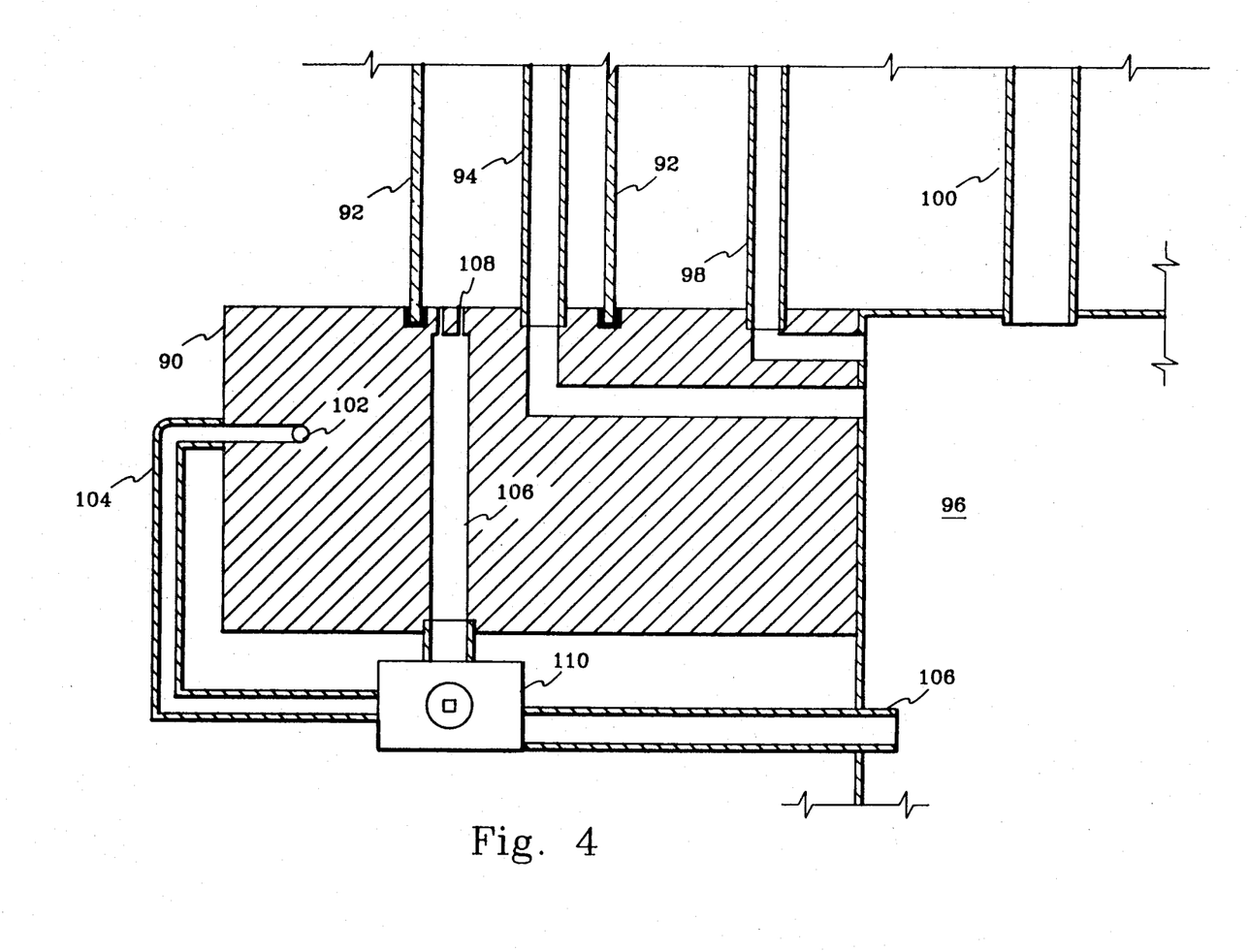
FIG. 4 is an end sectional view of the sampler of FIG. 1 taken perpendicular to the line of cylinders shown in FIG. 1 and through the center of one cylinder.

Referring now to FIG. 4 which is a section through the metal block perpendicular to the line of cylinders and passing through the center of one of the cylinders. The metal block is designated by 90 and the cylinder by 92. As shown, the overflow line 94 connects through metal block 90 with drain tank 96. Vent line 98 from the top closure of cylinder 92 also passes through the metal block and into drain tank 96. Drain tank 96 is vented to the atmosphere through line 100. Drain holes 108 from the bottom of cylinder 92 pass through the metal block into an enlarged drain 106 which enters three-way valve 110. Feed to the sampler enters block 90 through header 102 and feed line 104 which also connects with three-way valve 110. By appropriate operation of three-way valve 110, it is possible to close off the drain to tank 96 and flow sample feed through header 102, line 104, line 106 and lines 108 into cylinder 92. Three-way valve 110 can also be moved to block flow through line 104 and allow cylinder 92 to drain through lines 108 and 106. If desired, three-way valve 110 can be adjusted to allow flow of sample to cylinder 92 and drainage of liquid through line 106 to tank 96 at the same time. This allows for very precise control over the rate at which the feed sample is introduced to cylinder 92, and if desired, the rate at which liquid is drained from the cylinder upon completion of the sampling operation.

Figure 5:
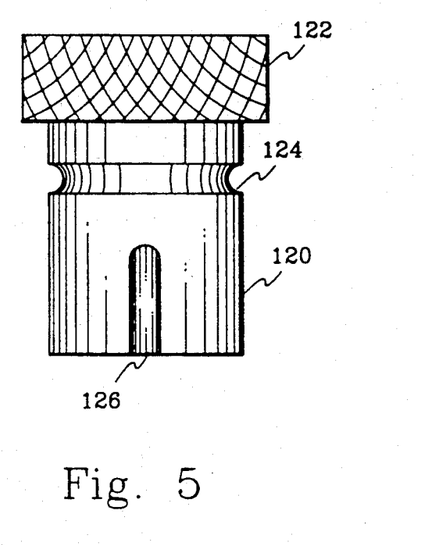
FIGS. 5 and 6 two views of the pressure relief plug in the top cover of each cylinder illustrated in FIGS. 1 and 2.
Figure 6:
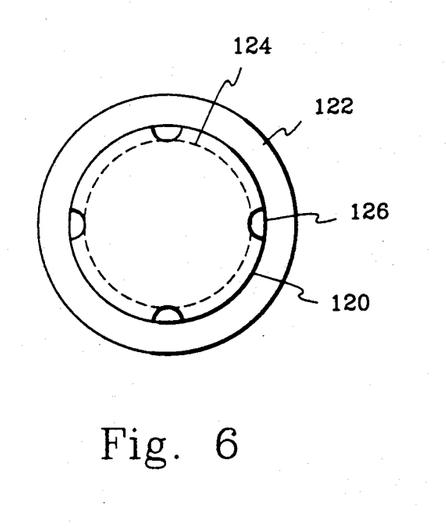

FIGS. 5 and 6 show, respectively, a side view and a bottom view of the pressure relief plug which is placed in the top cover of each cylinder. The pressure relief plug 120 contains a top portion 122 of larger cross-section which serves as a handle for the plug and which may be grasped to manually remove the plug from the cylinder cover. In the top portion of the plug is a recess 124 which is continued around the circumference of the plug and is designed to receive a ring gasket, usually of a rubber type material. The plug is fluted from the bottom up to a point short of recess 124. In FIG. 6, the flutes are shown as oval or semi-circular, however, they may be of any shape. Also, the flutes or grooves are shown of constant cross-section, however, they may be larger in cross-section at the bottom than at the top. The purpose of the flutes is to gradually reduce the pressure moving the plug from the cylinder cover as the plug is ejected. While FIG. 6 shows a plug with four flutes, any number of flutes may be used. The plug is designed to release from the cylinder cover at a relatively low pressure, usually between about 5 and about 10 psi. In any event, the release pressure is substantially less than any pressure which would damage the sampler and in particular the cylinders for holding the samples. The pressure relief plug is preferably slightly tapered from the top to the bottom to allow easy insertion and removal. The plug is conveniently made from brass or bronze, however, other construction materials may be employed.

The following examples are presented in illustration of various aspects of the invention.

EXAMPLE 1

Tests were carried out with a sampler of the design shown in FIG. 1. The sampler was installed in a small metal building and was vented through the back of the building and up to a point above the roof. Benzene monitors were placed in and around the sample building. Unleaded gasoline having a gravity of 61.8 and a vapor pressure of 9.6 was run through each of the five tubes of the sampler at the same time. The gasoline was introduced to the cylinders continuously for a period of 8 hours and 50 minutes. By gauging the products sump, it was calculated that the run consumed approximately 136 gallons of gasoline through the sampler. This is equivalent of taking one quart sampling of gasoline every minute for approximately 9 consecutive hours. Along with the benzene monitors, air samples were also pulled with an Enmet pump number 90001.000 (Model 42.CFR.84) using four benzene detector tubes. None of the benzene monitors showed any signs of benzene. Also, none of the four test tubes run indicated any benzene in the sample building including one which was pulled from under a bucket positioned over the sampler vent.

EXAMPLE 2

To determine the effectiveness of the brass pressure relief valves, five of these valves (one from each cylinder closure) were tested in a pressure apparatus to determine the pressure at which they would relieve the cylinders. The five plugs were actuated to relieve pressure at 7.0, 6.75, 7.0, 7.0, and 7.25 psi respectively. This compares very favorably with the 125 pound pressure rating of the cylinders used in the sampler.

OPERATION OF THE SAMPLER

The operation of the sampler may be described is conjunction with FIGS. 1 and 4. Referring to FIG. 1, a liquid pipeline product is transferred to the sample apparatus through line 32. The line pressure as evidenced by gauge 34 is 300 psi. Valve 36 is opened, partially, permitting flow of one pipeline liquid into block 2 with the rate being controlled to lower the pressure (shown by gauge 38) to the desired level. Usually when the sampler is on operation, the pressure in the block is essentially 0 psig. The temperature of the pipeline product liquid as measured by thermometer 40 is 75° F. Referring now to FIG. 4, the liquid product passes into header 102 and through tubing 104' and three-way valve 110 into nipple 106 and small orifices 108 and thereafter into the bottom of cylinder 92. Valve 110 is adjusted to assure overflow of liquid continuously through overflow pipe 94 to drain tank 96. In thus manner, the rate at which liquid is introduced to cylinder 92 ca- be controlled as desired. Referring back to FIG. 1, product sample is allowed to enter each of the five cylinders. When the sample height in each cylinder reaches the top of overflow pipe 18, the sample overflows and is removed from the bottom of the overflow pipe and discharged into drain tank 22. This allows a constant level to be maintained in the upper portion of each of cylinders 4. The flow of liquid into overflow pipes 18 and out of the system causes an aspirating effect whereby vapors in the cylinders are removed through the overflow pipes. In addition, the aspirating effect is such that air is pulled into the cylinders from the atmosphere through vent lines 20 via vent line 26. This operation assures that no vapors which accompany the product sample are in any way released to the atmosphere and brought in contact with the operator of the sampler.

After the operator has ascertained by reading the hydrometers, (not shown), what product, is being sampled, he further examines the product to determine that it has the correct color and gravity and that it is not contaminated with solids. At this point, the test is complete and feed to the sampler is discontinued by closing valve 36. Thereafter, each of the three-way valves 110 (FIG. 4) are opened to allow the samples to drain from cylinders 4 into drain tank 22.

The sampler described in Example 1 was constructed from a single block of stainless steel and stainless steel was also used in the various lines, connections three-way valves, and drain tank of this sampler.

The block used in the sampler was 22 inches long by 2 inches high by $4\frac{1}{2}$ inches deep. Five glass cylinders were installed on the block $3-\frac{1}{2}$ inches apart and were held down with $\frac{1}{4}$ inch rods screwed into the block. These rods also served to hold the cover used to seal the top of each cylinder. The cylinders which were made of glass were 2 inches in diameter and $22-\frac{1}{4}$ inches high. The cover for each cylinder was $3-\frac{1}{2}$ inches in diameter and 1 inch deep. Each cover was grooved on the underside to fit over the cylinder and provide a tight seal with a rubber gasket material. Each cylinder was fitted into a gasket material contained in a circular recess in the top of the metal block. Each cylinder cover $1-\frac{1}{4}$ inch opening in the top which was of sufficient size to introduce an hydrometer to the cylinder. The opening in each cover was sealed with a bronze pressure relief plug having an inside diameter of 1.24 inches. Each plug was $1-\frac{3}{8}$ inches long which included a $\frac{3}{8}$ inch serrated top having a diameter of $1-\frac{1}{2}$ inches which was used to insert and remove the plugs for insertion of an hydrometer. Each plug contained three equally spaced flutes having a depth of $\frac{1}{4}$ inch and a length of 0.625 inches measuring from the bottom of the plug. Each plug also contained a circumferential slot having a width of 0.155 inches and a depth of 0.12 inches. This slot which contained a neoprene ring gasket was located above the flutes.

The feed header was provided by drilling a 7/16 inch hole lengthwise through the front of the metal block. Five 7/16 inch holes were drilled through the front of the block into the header to provide communication with the sample feed lines which were constructed of $\frac{1}{4}$ inch tubing. The overflow line in each cylinder was constructed of $\frac{1}{2}$ inch tubing and extending upwardly in the cylinder for a distance of 14 inches. A $\frac{1}{4}$ inch vent line was connected with each cylinder through the cylinder cover. Both overflow lines and vent lines were open to the drain tank through passageways in the metal block.

The drain tank was positioned with its top flush with the top of the metal block and measured 22 inches wide by $3-\frac{1}{2}$ inches deep by 10 inches high. The drain tank was held to the metal block by suitable connections at the points where the vent lines and overflow lines connected with the drain tank through the metal block. The drain tank contained a lid which was affixed to the tank by screws and sealed with a gasket material.

Four 3/16 inch holes were provided under each cylinder for filling and draining the cylinder. The 3/16 inch drain holes opened into a single drain hole of 23/32 inches diameter which was connected by a $\frac{1}{2}$ inch pipe nipple to a $\frac{1}{2}$ inch three way ball valve. Each feed line was also connected to the three way valve. The outlet from each three way valve was connected by $\frac{1}{2}$ inch pipe nipple to the drain tank. The drain tank contained a 1 inch opening in the bottom for draining liquid and entrained gases from the cylinders and two $\frac{1}{2}$ inch openings in the top for connection with vent lines to the atmosphere.

Pressure gauges and a temperature indicator were positioned in the sample feed line and the metal block, as shown in FIG. 1 of the drawings.

The total weight of the sampler was 105 pounds. This provided an apparatus which could easily be moved from one location to another, depending on the need.

The type of construction described enables the sampler to be kept clean without great effort and the stainless steel is resistant to the atmosphere and other elements to which it is exposed. The use of a solid block provides the advantage of minimizing the number of connections which are required in the unit, thus reducing the likelihood of leakage. The block construction and attached drain tank also makes it possible to construct a sampler which is compact in size and is readily transported from one location to another.

The block construction, of course, is not limited to stainless steel, for example, the block could be made from other metals or from a machinable and drillable plastic material resistant to the various products to be sampled. Similarly, the various lines and fittings could also be made from plastic materials or from metals other than stainless steel.

While the block construction is preferred from the viewpoint of minimizing the size of the sampler and reducing the possibility of leakage, it is within the scope of the invention to use a hollow housing in place of the block and provide appropriate lines and connections within such housing to effect feed, drainage, and venting of the cylinders. Glass is used as the cylinder composition in the sampler of Example 1, however, it is within the scope of the invention to use other clear or transparent materials such as plastic materials in place of glass.

The use of cylinders for holding the samples is preferred because of their strength and ease of manufacture. It is within the scope of the invention, however, to use holders of other shapes as long as visual inspection of the samples is provided. Because of the difficulty in drilling long holes through a metal block, namely, the header for introducing feed to the cylinders, there is a limit as to how many cylinders can be placed on a block. It is possible to increase the available cylinders by attaching together two blocks and providing for feed of samples to each block. This type of arrangement would also allow for simultaneous sampling of products from two sources (pipelines) in a single portable test unit.

The invention has been particularly described in its application to sampling petroleum products from a pipeline. It can also find use in sampling liquids in petroleum refineries, gas plants, chemical plants or in any other installation where visual examination of a plurality of liquids is desired.

While certain embodiments and details have been shown for the purpose of illustrating the present invention, it will be apparent to those skilled in the art that various changes and modifications may be made herein without departing from the spirit or scope of the invention.

We claim:

1. A vapor tight multi-liquid sampler which comprises:
   (a) a rigid housing,
   (b) a plurality of transparent sample holders vertically disposed and spaced apart and secured on top of the rigid housing, each sample holder having a removable closure on top and being sealed to the top of the rigid housing,
   (c) a pressure relief plug in each said removable closure for relieving pressure,
   (d) a vent line for venting gas from each sample holder,
   (e) lines for feeding liquid sample to each sample holder and for draining liquid from each sample holder,
   (f) overflow tubes for removing excess liquid from each sample holder with aspiration of gas to prevent overfilling; and
   (g) valves to control the rate of sample feed to each sample holder and to control the rate of draining from each sample holder.

2. The sampler of claim 1 in which the vent lines, drain lines and overflow tubes are connected to a drain tank adjacent said rigid housing, wherein said drain tank contains a vent to the atmosphere and a liquid outlet to a separator or drain.

3. The sampler of claim 2 in which the plug in each removable closure for relieving pressure is a solid plug which is fluted from the lower end toward the top to provide a gradual release of pressure when the plug is expelled by pressure from the removable closure.

4. The sampler of claim 1 in which the functions of the valves in subparagraph (g) are performed by a single three-way valve which controls both sample feed to each transparent sample holder and sample draining from each transparent sample holder, said single three-way valve being capable of feeding or draining or simultaneous feeding and draining.

5. The sampler of claim 1 in which each transparent sample holder contains a hydrometer designed to reflect the gravity of a specific liquid sample.

6. A vapor tight multi-liquid sample which comprises:
   (a) a solid block containing a longitudinally disposed header which is plugged at one end of the block and is open at the other end to receive liquid samples,
   (b) a plurality of transparent cylinders vertically disposed and spaced apart and held on top of the solid block, each cylinder being closed with a removable closure on the top and being sealed to the block with a gasket on the bottom,
   (c) an opening in each removable cylinder closure of sufficient size to pass a hydrometer into and out of the cylinder; each said opening containing a pressure release plug,
   (d) a drain tank adjacent the solid block containing a liquid outlet to a separator or drain and a vent line to the atmosphere,
   (e) a vent line in the top closure of each cylinder and an overflow tube within each cylinder, the top of which terminates below the top of the cylinder, said overflow tube and vent line being connected to said drain tank,
   (f) openings in the block below each cylinder for draining the cylinders of liquid samples and for introducing liquid samples to the cylinders,
   (g) a sample feed line connecting each cylinder with the longitudinal header,
   (h) a line connecting the drain line from each cylinder with the drain tank; and
   (i) a three-way valve in each sample feed line connecting with each drain line from the cylinders so that each cylinder can be filled, drained or simultaneously filled and drained at variable rates with a single valve.

7. The sampler of claim 6 in which each cylinder contains a hydrometer designed to reflect the gravity of a specific liquid sample.

8. The sampler of claim 6 in which the solid block, feed lines, overflow tubes, cylinder closures, vent lines, drain lines and three-way valves are constructed of stainless steel.

9. The sampler of claim 8 in which the cylinders are constructed of glass.

10. The sampler of claim 6 in which the pressure release plug is a solid brass plug which is fluted from the lower end toward the top to provide a gradual release of pressure when the plug is expelled by pressure from the removable closure.

11. The sampler of claim 6 in which the drain tank is attached to the solid block.

12. A process for protecting an operator from exposure to vapors while evaluating a liquid sample containing such vapors, which comprises
  (1) continuously introducing a liquid sample containing vapors into the lower portion of a transparent vertically disposed vapor tight sampler zone,
  (2) overflowing said liquid into the upper portion of an aspirating zone vertically disposed within the sampler zone whereby a liquid level is maintained in the sampler zone with a vapor space above said liquid level, said aspirating zone being of lesser cross-section and shorter than the sample zone and said aspirating zone communicating with the sampler zone only at said upper portion;
  (3) flowing liquid from the lower portion of the aspirating zone to a drain zone which is vented to the atmosphere and which separately communicates with the vapor space of the sampler zone, whereby liquid overflowing into the aspirating zone aspirates vapors and air from the vapor space of the sampler zone, and
  (4) visually and by measurement determining desired properties of the liquid sample.

13. The process of claim 12 which includes a plurality of sampler zones.

14. The process of claim 13 in which the liquid sample is selected from the group consisting of gasoline, jet fuel and diesel fuel taken from a pipeline.

15. The process of claim 14 in which a different gravity range is measured in each sampler zone to identify the liquid sample.

16. The process of claim 12 in which liquid and vapors which enter the drain zone are passed by one way flow to a separator zone.

17. The process of claim 16 in which the liquid sample is obtained from a source selected from the group consisting of petroleum refineries, gas plants and chemical plants.

* * * * *